United States Patent
Katayama et al.

(10) Patent No.: US 7,271,275 B2
(45) Date of Patent: Sep. 18, 2007

(54) PROCESS FOR PRODUCING A FATTY ACID ESTER

(75) Inventors: Takanobu Katayama, Wakayama (JP); Nobuhiro Tatsumi, Wakayama (JP); Osamu Tabata, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/962,486

(22) Filed: Oct. 13, 2004

(65) Prior Publication Data
US 2005/0113589 A1    May 26, 2005

(30) Foreign Application Priority Data
Oct. 14, 2003 (JP) .............................. 2003-353225

(51) Int. Cl.
*C11C 1/00* (2006.01)
(52) U.S. Cl. ..................................................... 554/169
(58) Field of Classification Search ................. 554/169
See application file for complete search history.

(56) References Cited

U.S. PATENT DOCUMENTS 4,698,186 A * 10/1987 Jeromin et al. ............. 554/174
5,849,939 A * 12/1998 Mittelbach et al. ......... 554/169
2002/0062035 A1 * 5/2002 Tatsumi et al. ............. 554/124

FOREIGN PATENT DOCUMENTS

| DE | 19600025 A1 | 7/1997 |
| EP | 1211236 A1 | 6/2002 |
| JP | 3-115249 A | 5/1991 |
| JP | 2002-346392 A | 12/2002 |

OTHER PUBLICATIONS

JAPIO translation of JP-07/224002, 1995.*

* cited by examiner

*Primary Examiner*—Deborah D. Carr
(74) *Attorney, Agent, or Firm*—Birch, Stewart, Kolasch & Birch, LLP

(57) ABSTRACT

The present invention relates to a process for producing a fatty acid ester by using a fatty acid and an alcohol as starting materials, including reducing the acid value of a raw material supplied to a catalyst layer to an acid value lower than the acid value of a raw material fatty acid and then esterifying the raw material in the presence of a solid catalyst.

3 Claims, 1 Drawing Sheet

PROCESS FOR PRODUCING A FATTY ACID ESTER

FIELD OF THE INVENTION

The present invention relates to a process for producing a fatty acid ester.

BACKGROUND OF THE INVENTION

Fatty acid esters are important materials as raw materials for producing higher alcohols and oil and fat chemical products such as ester sulfonates and alkanolamides. These fatty acid esters are generally obtained by a reaction between a triglyceride and a lower alcohol or a reaction between a fatty acid and a lower alcohol. Various solid catalysts have been developed for esterification reactions between fatty acids and lower alcohols. Examples of the solid catalyst include such as cation exchange resins, single or complex metal oxides, stabilized acids and synthesized zeolite. There is the method described in JP-A 3-115249 as an example in which such a solid acid catalyst is applied to the production of a fatty acid ester.

Further, the improvement and development of these solid catalysts are still ongoing. For example, JP-A 2002-346392 discloses a solid acid catalyst made of an improved cation exchange resin.

SUMMARY OF THE INVENTION

The present invention relates to a process for producing a fatty acid ester by using a fatty acid and an alcohol as starting materials, including reducing the acid value of a raw material supplied to a catalyst layer to an acid value lower than the acid value of a raw material fatty acid in advance and then esterifying the raw materials in the presence of a solid catalyst.

DETAILED DESCRIPTION OF THE INVENTION

Figure 1:
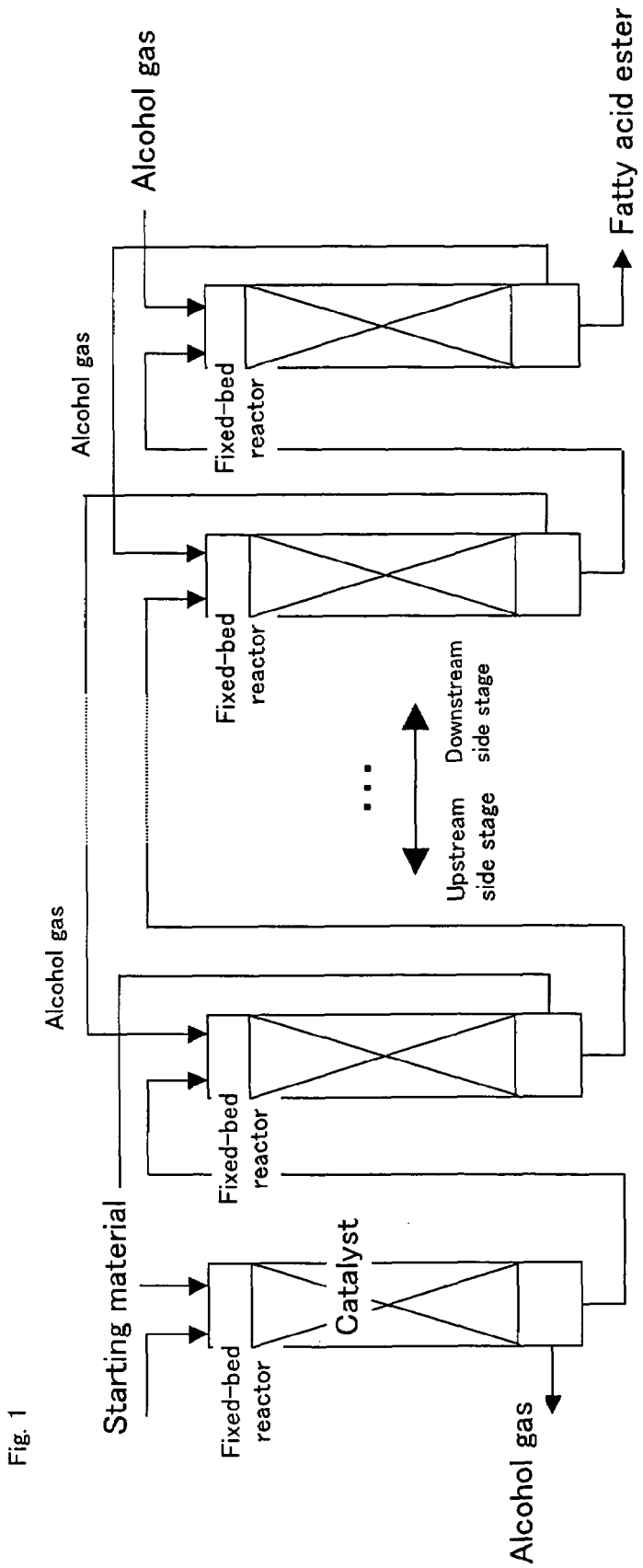
FIG. 1 shows a reaction flow of an example of the invention.

JP-A 3-115249 discloses a system in which a Fixed-bed reactor packed with a solid acid catalyst is used to circulate a fatty acid put in a liquid state and a lower alcohol in a gaseous state. However, there is the problem that since the fatty acid supplied as the raw material is an organic acid, the solid acid catalyst is partly dissolved in the fatty acid or is reduced in catalytic activity when used for a long period of time. There is also the problem that the strength required for the solid catalyst is dropped by the dissolution of components constituting the catalyst in the fatty acid.

JP-A 2002-346392 made various improvements of a solid catalyst as to a reduction in the ability of an esterifying catalyst. However, these improvements were still insufficient.

The present invention relates to a process for producing a fatty acid ester efficiently from a fatty acid and an alcohol by suppressing the dissolution and falling of a catalyst component used in a reaction without decreasing the activity and strength of the catalyst.

According to the present invention, a fatty acid ester can be obtained efficiently by suppressing the dissolution and falling of a catalyst component used in a reaction and without decreasing the activity and strength of the catalyst.

Though no particular limitation is imposed on the raw material fatty acid used in the present invention, examples of the fatty acid include saturated or unsaturated fatty acids obtained by hydrolysis of natural vegetable oil and fats and animal oil and fats. These fatty acids may be those having a single alkyl chain length or a mixture of fatty acids having different alkyl chain lengths. Examples of the vegetable oil and fats include coconut oil, palm oil, palm kernel oil, soybean oil and rape seed oil. Examples of the animal oil and fats include beef tallow, lard and fish oils. Examples of the fatty acid further include organic acids such as dicarboxylic acids and carboxylic acids. These fatty acids are preferably used in a liquid state.

Although no particular limitation is imposed on the alcohol used in the present invention, lower alcohols having 1 to 5 carbon atoms are desirable. Specific examples of the alcohol include such as methanol, ethanol and propanol. Among these compounds, methanol is desirable in view of low cost and recovery easiness in the case of using it as an industrial raw material.

In the present invention, the acid value of the raw material supplied to the catalyst layer means the acid value of all components excluding alcohols and water to be supplied to the catalyst layer. Examples of a method of decreasing the acid value of the raw material to be supplied to the catalyst layer in the present invention include such as (1) a method in which a fatty acid ester is added to the raw material fatty acid and (2) a method in which a fatty acid is reacted with an alcohol in the presence of no catalyst to esterify partially before an esterification reaction is run before an esterification reaction run in the presence of a catalyst (hereinafter referred to as a pre-reactor method). These methods may be combined.

Any material may be used as the fatty acid ester to be added to the raw material fatty acid without any particular limitation in the method (1) insofar as it does not inhibit the esterification reaction in the reactor or does not deteriorate the catalyst activity. Commercially available fatty acid esters may be used and it is also a particularly preferable embodiment on an industrial level to add a fatty acid ester obtained in the production process of the present invention partly to the raw material fatty acid.

As to a reaction system in the pre-reactor in the method (2), the reaction may be run in a continuous system, batch system or semi-continuous system. In the continuous system, a packed column, a wetted wall column, a continuous stirring vessel type reactor (CSTR) or the like may be used. In the batch system or semi-continuous system, for example, a reaction vessel with a stirrer is used. Also, these systems may be combined.

As to a reaction system when the pre-reactor method is carried out in a Fixed-bed system, the alcohol may be put in a gas or liquid state and the fatty acid may be used in a liquid state. These reaction raw materials maybe used in any of the reaction systems including a gas-liquid co-current system and a gas-liquid counter current system. A contact system in the case of a liquid-liquid system may be either co-current downflow or co-current upflow. As the packing in the case of the Fixed-bed system, any material may be used insofar as it is a material which is not corroded by the raw material fatty acid. Examples of the packing to be used include SUS balls, ceramic balls and Raschig ring. These packings may be regular packings or irregular packings.

The reaction temperature in the pre-reactor method is usually 100 to 300° C. and more preferably 150 to 220° C.

from the viewpoint of progressing the reaction sufficiently and suppressing the generation of byproducts. The liquid space velocity (LHSV) based on the fatty acid in the case of using a Fixed-bed reactor is usually preferably 0.02 to 5.0/hr and more preferably 0.5 to 3.0/hr from the viewpoint of suppressing a reduction in productivity, obtaining a sufficient reaction rate and dropping the acid value to a desired one. The molar ratio of the alcohol to the fatty acid is preferably 1.5 to 30 times, more preferably 1.5 to 10 times and even more preferably 1.5 to 5 times the stoichiometrically necessary amount from the viewpoint of raising the reaction rate and suppressing the amount of the alcohol to be recovered.

These methods of reducing acid value may be carried out by properly combining them according to the need.

Although in the present invention, the preferable acid value of the raw material supplied to the catalyst layer cannot be said in a wholesale manner because it is determined according to the type of fatty acid, the type of solid catalyst to be used and productivity, the ratio of the acid value of the raw material supplied to the catalyst layer to that of the raw material fatty acid is designed to be preferably 90% or less, more preferably 80% or less, even more preferably 60% or less and even more preferably 40% or less from the viewpoint of restricting the concentration of the fatty acid supplied to the catalyst layer and preventing a reduction in the strength of the catalyst. A specific acid value of the raw material supplied to the catalyst layer is preferably 240 mg-KOH/g or less, more preferably 220 mg-KOH/g or less, even more preferably 200 mg-KOH/g or less and even more preferably 150 mg-KOH/g or less. As to the lower limit of the acid value, the ratio of the acid value of the raw material supplied to the catalyst layer to that of the raw material fatty acid is designed to be preferably 2.5% or more, more preferably 10% or more and even more preferably 20% or more from the viewpoint of preventing an increase in the amount to be circulated and preventing a rise in the temperature necessary to run a reaction when using a pre-reactor. The specific acid value is preferably 10 mg-KOH/g or more, more preferably 30 mg-KOH/g or more and even more preferably 50 mg-KOH/g or more.

The acid value of the raw material supplied to the catalyst layer is made to be preferably as low as possible. However, in the case of considering actual installment, the acid value set to a lower one, on the other hand, leads to a reduction in productivity and/or large-scaled equipment both in the case of adding an ester and in the case of reacting in a pre-reactor. It is therefore necessary to set a desired acid value taking this into account.

In the present invention, the reaction system adopted when the raw material reduced in acid value is supplied to run an esterification reaction in the presence of a solid catalyst may be any system insofar as it runs a heterogeneous reaction. However, a system using a Fixed-bed reactor is preferable from the point that it is unnecessary to separate catalysts. In a reaction system using a Fixed-bed reactor, the alcohol is gasified to run a reaction in a gas-liquid-solid three-phase in general. However, a liquid-liquid-solid reaction system in which the alcohol is supplied in a liquid state may be adopted. The contact system in the case of a gas-liquid-solid reaction may be any reaction system of gas-liquid co-current and gas-liquid counter current. The contact system in the case of a liquid-liquid-solid reaction may be any of a co-current downflow system and a co-current upflow system. Also, in a gas-liquid-solid reaction, a system in which Fixed-bed reactors packed with a solid catalyst are arranged in a multistage and a gas-liquid counter current operation and a gas-liquid co-current operation are combined may be adopted. Also, a pseudo counter current operation may be carried out in which in a multistage co-current system, the fatty acid is supplied to a reactor on the upstream side and then fed to the downstream side stage, the gaseous alcohol is supplied to a reactor on the downstream side so as to allow a co-current downflow operation, the gaseous alcohol discharged from the outlet of the reactor is returned to the upstream side stage to repeat a co-current downflow operation in the Fixed-bed packed with a solid catalyst in each reactor. Among these reaction systems, the system in which a pseudo counter current operation is carried out is preferable.

As to the reaction pressure, the reaction is generally run under normal pressure or under pressure. However, the reaction may be run under reduced pressure. Under reduced pressure, a gas-liquid-solid reaction can be run at a temperature lower than the atmospheric boiling point of the alcohol to be used. Under pressure, a liquid-liquid-solid reaction can be run at a temperature more than the atmospheric boiling point.

The reaction temperature, though it depends on the catalyst to be used, is generally preferably 50 to 250° C., more preferably 60 to 220° C. and even more preferably 80 to 200° C. from the viewpoint of obtaining sufficient reactivity, raising reaction speed and suppressing the production of byproducts.

The liquid space velocity (LHSV) based on the fatty acid in the case of using a Fixed-bed reactor is generally preferably 0.02 to 5.0/hr and more preferably 0.5 to 3.0/hr from the viewpoint of economy and also from the viewpoint of obtaining a sufficient reaction rate and raising the purity of a fatty acid ester to be produced.

The molar ratio of the alcohol to the fatty acid is preferably 1.5 to 30 times, more preferably 1.5 to 10 times and even more preferably 1.5 to 5 times the stoichiometrically necessary amount from the viewpoint of raising the reaction rate and suppressing the amount of the alcohol to be recovered.

In the present invention, esterification is carried out in the presence of a solid catalyst. Examples of the solid catalyst used in the present invention include such as single or complex metal oxides, metal sulfates, metal phosphates, metal phosphonates, stabilized acids which are supported on or fixed to a support, natural minerals and layer compounds, ultra-strong acids, synthetic zeolite and ion exchange resins. Examples of the single or complex metal oxides include niobic acid and $SiO_2$—$Al_2O_3$ and $SiO_2$—$ZrO_2$. Examples of the metal sulfates include $Al_2(So_4)_x \cdot H_2O$. Examples of the metal phosphates include $FePO_4$ and $AlPO_4$. Examples of the metal phosphonates include aluminum phenylphosphonate. Examples of the stabilized acids which are supported or fixed on a support include sulfuric acid ion-carrying $ZrO_2$ and $TiO_2$. Examples of the natural minerals and layer compounds include acid clay, kaolin and montmorillonite. Examples of ultra-strong acids include sulfone fluoride resins (e.g., Naphyon manufactured by Du Pont K.K.). Examples of the synthetic zeolite include ZCP-50 manufactured by Shokubai Catalysts & Chemicals Industries Co., Ltd. Examples of the ion exchange resin include cation exchange resins such as High Porous Cation Resin RCP-160H. Also, a weak-acidic solid catalyst as described below may be used.

A preferable group of the weak acidic solid catalyst used in the present invention is those having a strong acidic point of 0.2 mmol/g-Cat or less, which point is defined below and a weak acidic point of 0.3 mmol/g-Cat or more, which point is defined below.

Weak acidic point: A point where $NH_3$ is dissociated at a temperature range from 100 to 250° C. in TPD (ammonia-adsorption-desorption method).

Strong acidic point: A point where $NH_3$ is dissociated at a temperature higher than 250° C. in TPD.

Examples of a preferable group among these weak acidic solid catalysts include molded articles of weak acidic solid catalysts having the following structure (A) or (B) and metal atom (C).

Structure (A): Structure obtained by eliminating a hydrogen atom from at least one OH group which an inorganic phosphoric acid has.

Structure (B): Structure obtained by eliminating a hydrogen atom from at least one OH group which an organic phosphoric acid represented by the formula (1) or (2) has.

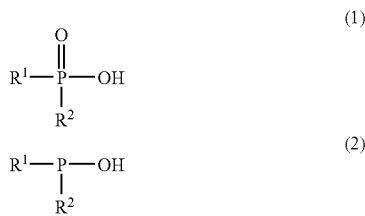

In the formula, $-R^1$ and $-R^2$ are respectively selected from —R, —OR, —OH and —H, where at least one of $-R^1$ and $-R^2$ is —R or —OR, provided that —R is an organic group having 1 to 22 carbon atoms.

Metal atom (C): One or more metal atoms selected from aluminum, gallium and iron.

Examples of the inorganic phosphoric acid in the above structure (A) include condensed phosphoric acids such as orthophosphoric acid, methaphosphoric acid and pyrophosphoric acid. Orthophosphoric acid is preferable in view of performance. Examples of the organic phosphoric acid in the above structure (B) include phosphonic acid, monophosphonate, phosphinic acid, monophosphate, diphosphate, monophosphite and diphosphite. Mixtures of these compounds may be used and phosphonic acid is preferable.

As the organic group—R in the organic phosphoric acid, alkyl groups such as methyl, ethyl, n-propyl, iso-propyl, n-butyl, iso-butyl, tert-butyl, n-hexyl, 2-ethylhexyl, octyl, dodecyl and octadecyl and aryl groups such as phenyl and 3-methylphenyl. These groups with which an amino group, alkoxy group, carbonyl group, alkoxycarbonyl group, carboxylic acid group, halogen group such as a chloro group, phosphonic acid group or sulfonic acid group is bound are also used.

As the metal atom (C), aluminum is preferable in view of performance and/or cost. The metal atom (C) may contain a small amount of metal atoms other than aluminum, gallium and iron to improve selectivity and other abilities. All metal atoms (C) contained in the catalyst is not necessarily required to combine with the structure (A) or (B), but a part of the metal atom (C) may exist in the form of a metal oxide or a metal hydroxide.

Examples of other groups preferable as the weak acidic solid catalyst in the present invention include molded articles of solid catalysts containing aluminum orthophosphate. Those having a pore diameter of 6 to 100 nm, a pore volume of 0.46 ml/g or more and an acid amount of 0.40 mmol/g are preferable.

As a method of preparing the weak acidic solid catalyst in the present invention, a precipitation method, a method of impregnating a metal oxide or a hydroxide with an inorganic or organic phosphoric acid or a method of substituting an organic phosphoric acid group for an inorganic phosphoric acid group in an inorganic aluminum phosphate gel are used. The precipitation method is preferable.

Also, when preparing the catalyst of the present invention, it is possible that a carrier having a high surface area is made to exist to obtain a carrier catalyst. As the carrier, silica, alumina, silica alumina, titania, zirconia, diatomaceous earth, activated carbon or the like may be used. If the carrier is used in an excessive amount, the content of an active component is decreased, causing reduced activity and the proportion of the carrier in the catalyst is therefore preferably 90% by weight or less.

EXAMPLES

The following examples further describe and demonstrate embodiments of the present invention. The examples are given solely for the purpose of illustration and are not to be construed as limitations of the present invention.

Production Example 1 of a catalyst (aluminum phosphate catalyst)

Aluminum nitrate and orthophosphoric acid were used to make an aqueous solution containing these components (mol ratio: 1:1) and aqueous ammonia was added dropwise to the solution at 40° C. until the solution was adjusted to pH 7 to obtain a precipitate, which was then dried at 110° C. and crushed. 10% by weight of alumina sol was added to the crushed catalyst. The crushed catalyst was then extrusion-molded under a load of about 2 MPa and then calcinated at 400° C. for 3 hours to obtain a molded catalyst having a diameter of 1.7 mmφ and a length of 4 to 6 mm.

Production Example 2 of a catalyst (aluminum phosphate catalyst)

Aluminum nitrate and orthophosphoric acid were used to make an aqueous solution containing these components (mol ratio: 1:1) and aqueous ammonia was added dropwise to the solution at 40° C. until the solution was adjusted to pH 7 to obtain a precipitate, which was then dried at 110° C. and crushed. 2% by weight of graphite was added to the crushed catalyst. The crushed catalyst was then tablet-molded under a load of about 25 MPa, then dried at 120° C. for 3 hours and then calcinated at 400° C. for 3 hours to obtain a molded catalyst having a cylindrical form, a diameter of 3.0 mmφ and a height of 3.0 mm.

Production Example 3 of a catalyst (ethylphosphonic acid addition aluminum phosphate catalyst)

Ethylphosphonic acid, 85% orthophosphoric acid and aluminum nitrate (nonahydrate) were dissolved inamol ratio of 1:2.7:3.3 in 1000 g of water. An aqueous ammonia solution was added dropwise to the mixed solution at ambient temperature to raise the pH of the solution to 5. The generated gel-like white precipitate was filtered, washed with water and dried at 110° C. for 15 hours. The precipitate was crushed into a size of 60 mesh or less and then, 10% by weight of alumina sol was added to the crushed catalyst. The crushed catalyst was then extrusion-molded under a load of about 2 MPa and then calcinated at 250° C. for 3 hours to obtain a molded catalyst having a diameter of 1.7 mmφ and a length of 4 to 6 mm.

Example 1

A reactor having an inside diameter of 35.5 mmφ and a length of 800 mm and provided with a multipoint temperature gage having an inside diameter of 4 mmφ in the center thereof was packed with 300 ml of molded articles of aluminum phosphate obtained in Production Example 1 and having a diameter of 1.7 mmφ as a catalyst such that the packed density was 0.456 g/ml. A mixed solution (concentration of aluminum: less than 1 mg/kg) prepared by adding a methyl ester (mixed solution of 85% of methyl laurate and 15% of methyl palmitate) to a fatty acid mixture (acid value=270 mg-KOH/g) of 75% of lauric acid and 25% of palmitic acid such that the acid value was 20 mg-KOH/g was supplied from the top of the reactor at a LHSV of 2.0/hr. Methanol was supplied from the top of the reactor in a mol ratio of 5 to the fatty acid mixture to carry out a gas-liquid co-current operation. The reaction pressure was adjusted to 0.5 MPa. The system was heated by an electric heater such that the reaction temperature was 150° C. After the weight of the raw material to be flowed reached 1500 times the weight of the packed catalyst, the reaction solution was sampled. Methanol was removed by distillation from the resulting reaction solution and then, the concentration of metals dissolved in the reaction solution was measured, to observe no dilution of metals. The reaction condition and results are shown in Table 1.

Example 2

The reaction was run in the same manner as in Example 1 except that the reaction temperature was changed to 200° C. After the weight of the raw material to be flowed reached 1300 times the weight of the packed catalyst, the reaction solution was sampled. Methanol was removed by distillation from the resulting reaction solution and then, the concentration of metals dissolved in the reaction solution was measured, to observe no dilution of metals. The reaction condition and results are shown in Table 1.

Comparative Example 1

The reaction was run in the same manner as in Example 1 except that the fatty acid mixture (acid value=270 mg-KOH/g) of 75% of lauric acid and 25% of palmitic acid was used as it was without decreasing the acid value of the raw material. The concentrations of metals, namely, aluminum and phosphorous in the fatty acid mixture were respectively less than 1.0 mg/kg. After the weight of the raw material to be flowed reached 1600 times the weight of the packed catalyst, the reaction solution was sampled. Methanol was removed by distillation from the resulting reaction solution and then, the concentration of metals dissolved in the reaction solution was measured, to observe a dilution of metals. The reaction condition and results are shown in Table 1.

TABLE 1

|  | Example 1 | Example 2 | Comparative example 1 |
| --- | --- | --- | --- |
| Acid value of the raw material supplied to the catalyst layer (mg-KOH/g) | 20 | 20 | 270 |
| [(Acid value of the raw material supplied to the catalyst layer)/ (Acid value of the raw material fatty acid)] × 100 (%) | 7.4 | 7.4 | 100 |

TABLE 1-continued

|  | Example 1 | Example 2 | Comparative example 1 |
| --- | --- | --- | --- |
| Catalyst | Alminum phosphate | Alminum phosphate | Alminum phosphate |
| Amount of the catalyst (ml) | 300 | 300 | 300 |
| LHSV (1/hr) | 2.0 | 2.0 | 2.0 |
| Methanol/Raw material fatty acid mixture (mol ratio) | 5.0 | 5.0 | 5.0 |
| Reaction temperature (° C.) | 150 | 200 | 150 |
| Liquid throughput (g-raw material/g-catalyst) | 1500 | 1300 | 1600 |
| Metal concentration (mg/kg) | <1.0 | <1.0 | 7.5 |

Example 3

A reactor having an inside diameter of 13.0 mmφ and a length of 833 mmφ and provided with a multipoint temperature gage having an outside diameter of 3.18 mmφ in the center thereof was packed with 20 ml of molded articles of aluminum phosphate obtained in Production Example 2 and having a diameter of 3.0 mmφ and a height of 3.0 mm as a catalyst such that the packed density was 0.570 g/ml. The strength of the catalyst prior to a reaction was 4.6 DaN measured by a Kiya type hardness meter. A fatty acid methyl ester obtained in a reaction was added to a fatty acid mixture (acid value=270 mg-KOH/g) of 75% of lauric acid and 25% of palmitic acid to adjust the acid value to 180 mg-KOH/g. This mixture was supplied from the bottom of the reactor at a LHSV of 3.0/hr. Methanol was supplied from the bottom of the reactor in a mol ratio of 5 to the fatty acid mixture to carry out an upward gas-liquid co-current operation. The reaction pressure was adjusted to 1.0 MPa. The system was heated by an electric heater such that the reaction temperature was 200° C. After the weight of the raw material to be flowed reached 540 times the weight of the packed catalyst, the catalyst was withdrawn to measure the strength of the catalyst, to find that the strength of the catalyst was not changed, and a fatty acid methyl ester having an acid value of 13 mg-KOH/g was obtained. The reaction condition and results are shown in Table 2.

Comparative Example 2

The reaction was run in the same manner as in Example 3 except that the fatty acid mixture (acid value=270 mg-KOH/g) of 75% of lauric acid and 25% of palmitic acid was used as it was without decreasing the acid value of the raw material. After the weight of the raw material to be flowed reached 540 times the weight of the packed catalyst, the catalyst was withdrawn to measure the strength of the catalyst. The reaction condition and results are shown in Table 2. Although the acid value of the reaction product was the same as in Example 3, a reduction in the strength of the catalyst was found.

TABLE 2

|  | Example 3 | Comparative example 2 |
| --- | --- | --- |
| Acid value of the raw material supplied to the catalyst layer (mg-KOH/g) | 180 | 270 |
| [(Acid value of the raw material supplied to the catalyst layer)/ (Acid value of the raw material fatty acid)] × 100 (%) | 67 | 100 |

TABLE 2-continued

|  | Example 3 | Comparative example 2 |
|---|---|---|
| Catalyst | Alminum phosphate | Alminum phosphate |
| Amount of the catalyst (ml) | 20 | 20 |
| LHSV (1/hr) | 3.0 | 3.0 |
| Methanol/Raw material fatty acid mixture (mol ratio) | 5.0 | 5.0 |
| Reaction temperature (° C.) | 200 | 200 |
| Liquid throughput (g-raw material/g-catalyst) | 540 | 540 |
| Strength of the catalyst (DaN) | 4.6 | 0.9 |
| acid value of a reaction product (mg-KOH/g) | 13.0 | 13.0 |

Comparative Example 3

A reactor having an inside diameter of 35.5 mmφ and a length of 800 mm and provided with a multipoint temperature gage having an inside diameter of 4 mmφ in the center thereof was packed with 240 ml of 1.7-mmφ-diameter molded articles of aluminum phosphate to which ethylphosphonic acid was added and which was obtained in Production Example 3 as a catalyst such that the packed density was 0.534 g/ml. A fatty acid mixture (acid value=270 mg-KOH/g) of 75% of lauric acid and 25% of palmitic acid was supplied from the top of the reactor at a LHSV of 0.5/hr. Methanol was supplied from the top of the reactor in a mol ratio of 3 to the fatty acid mixture to carry out a gas-liquid co-current operation. The reaction pressure was adjusted to 1.0 MPa. The system was heated by an electric heater such that the reaction temperature was 180° C. The resulting reaction product was washed with 80° C. warm water and methanol was removed from the reaction product. The acid value of the resulting product was 57 mg-KOH/g. After the weight of the raw material to be flowed reached 100 times the weight of the packed catalyst, the activity of the catalyst was measured and then the strength of the catalyst was measured when the weight of the raw material to be flowed reached 220 times the weight of the packed catalyst. The reaction condition and results are shown in Table 3.

Example 4

A pre-reactor having an inside diameter of 35.5 mmφ and a length of 800 mm and provided with a multipoint temperature gage having an inside diameter of 4 mmφ in the center thereof was packed with 670 ml of 3-mmφ-SUS balls to run a non-catalyst reaction. A reactor having the same shape as that used in Comparative Example 3 and packed with the same catalyst that was used in Comparative Example 3 was connected to the pre-reactor such that the reaction product discharged from this pre-reactor was supplied to the reactor. The connected reactor was packed with 240 ml of the same catalyst that was used in Comparative Example 3 as a catalyst such that the packed density was 0.534 g/ml. The strength of the catalyst prior to a reaction was 0.9 DaN measured by a Kiya type hardness meter. A fatty acid mixture (acid value=270 mg-KOH/g) of 75% of lauric acid and 25% of palmitic acid was supplied from the top of the reactor packed with the SUS balls at a LHSV of 0.5/hr. Methanol was supplied from the top of the reactor in a mol ratio of 3 to the fatty acid mixture to carry out a gas-liquid co-current operation. The reaction pressure was adjusted to 1.0 MPa. The system was heated by an electric heater such that the reaction temperature was 180° C. The reaction product obtained from the reactor packed with SUS balls was washed with 80° C. warm water and methanol was removed from the reaction product. The acid value of the resulting product was 133 mg-KOH/g. The reaction mixture was supplied directly to the reactor packed with catalysts in the same condition. After the weight of the raw material to be flowed reached 100 times the weight of the packed catalyst, the activity of the catalyst was measured and then the strength of the catalyst was measured when the weight of the raw material to be flowed reached 220 times the weight of the packed catalyst. The reaction condition and results are shown in Table 3.

In Table 3, the evaluation of catalyst activity was made in the following method.

<Method of Evaluation of Catalyst Activity>

After the liquid throughput (g-raw material/g-catalyst) had reached the fixed number, the reaction solution was sampled at the outlet of the reactor. The obtained reaction product was washed with 80° C. warm water and methanol was removed from the reaction product. The acid value (hereinafter referred to as reaction product acid value) of the resulting product was measured to calculate the activity of the catalyst according to the following equation.

$$\text{Catalyst activity} = \ln[(\text{Acid value of raw material supplied to the catalyst layer} - \text{Equilibrium acid value})/(\text{Acid value of the reaction product} - \text{Equilibrium acid value})]$$

This reaction is a reversible reaction and therefore, an equilibrium value which the acid value will reach exists. The equilibrium acid value is a constant defined by a reaction condition and composition, and the equilibrium acid value used in this reaction is about 12 mg-KOH/g when, for example, the temperature is 200° C. and the mol ratio of methanol is 3.

TABLE 3

|  | Comparative example 3 | Example 4 |
|---|---|---|
| Acid value of the raw material supplied to the catalyst layer (mg-KOH/g) | 270 | 133 |
| Catalyst | Ethylphosphonic acid addition aluminum phosphate | Ethylphosphonic acid addition aluminum phosphate |
| Amount of the catalyst (ml) | 240 | 240 |
| LHSV (1/hr) | 0.5 | 0.5 |
| Methanol/Raw material fatty acid mixture (mol ratio) | 3.0 | 3.0 |
| Reaction temperature (° C.) | 180 | 180 |
| Strength of the catalyst when liquid throughput (g-raw material/g-catalyst) is 220 times (DaN) | 0.6 | 0.9 |
| Activity of the catalyst when liquid throughput (g-raw material/g-catalyst) is 100 times | 0.43 | 1.1 |

The invention claimed is:

1. A process for producing a fatty acid ester by using a fatty acid and an alcohol as starting materials, comprising reducing the acid value of a raw material supplied to a catalyst layer to an acid value lower than the acid value of the raw material fatty acid in advance and then esterifying the raw materials in the presence of a solid catalyst, by reacting the fatty acid with the alcohol in the presence of no catalyst for partial esterification before the esterification reaction in the presence of a catalyst, thereby decreasing the acid value of the raw material supplied to the catalyst layer to an acid value lower than that of the raw material fatty acid.

2. The process of claim 1, comprising returning part of the fatty acid ester obtained in the reaction to the raw material to circulating it for use, thereby decreasing the acid value of the raw material supplied to the catalyst layer to an acid value lower than that of the raw material fatty acid.

3. The process of claim 1, in which Fixed-bed reactors packed with a solid catalyst are formed in a multistage, the fatty acid is supplied to a reactor on the upstream side and then fed to the downstream side stage, the alcohol in the form of a gas is supplied to a reactor on the downstream side so as to allow a co-current downflow operation, and the gaseous alcohol discharged from the outlet of the reactor is returned to the upstream side stage to repeat a co-current downflow operation in the Fixed-bed packed with a solid catalyst in each reactor.

* * * * *